(12) United States Patent
White

(10) Patent No.: US 7,761,936 B2
(45) Date of Patent: Jul. 27, 2010

(54) THERAPEUTIC FLOOR MAT SYSTEM AND METHOD

(75) Inventor: Russell W. White, Austin, TX (US)

(73) Assignee: Affinity Labs of Texas, LLC, Frisco, TX (US)

( * ) Notice: Subject to any disclaimer, the term of this patent is extended or adjusted under 35 U.S.C. 154(b) by 857 days.

(21) Appl. No.: 11/063,209

(22) Filed: Feb. 22, 2005

(65) Prior Publication Data

US 2006/0185071 A1  Aug. 24, 2006

(51) Int. Cl.
*A47K 3/02* (2006.01)
(52) U.S. Cl. ......................................................... 4/581
(58) Field of Classification Search ............. 4/580–583; 15/215
See application file for complete search history.

(56) References Cited

U.S. PATENT DOCUMENTS

| | | | |
|---|---|---|---|
| 3,605,166 A * | 9/1971 | Chen | ............................ 15/215 |
| 4,207,141 A | 6/1980 | Seymour | |
| 4,512,044 A | 4/1985 | Clark | |
| 4,625,344 A | 12/1986 | Howard | |
| 4,697,292 A | 10/1987 | LaValley | |
| 4,934,000 A | 6/1990 | Freedman | |
| 5,028,007 A | 7/1991 | Wokal | |
| 5,069,951 A | 12/1991 | Egan | |
| 5,216,764 A | 6/1993 | Hall et al. | |
| 5,381,564 A | 1/1995 | Carroll | |
| 5,575,034 A | 11/1996 | Biernacinski et al. | |
| 5,599,426 A | 2/1997 | Hoffman | |
| 5,685,829 A | 11/1997 | Allen | |
| 5,781,941 A | 7/1998 | Radke et al. | |
| 5,939,088 A * | 8/1999 | Ito et al. | ...................... 424/414 |
| 6,014,779 A | 1/2000 | Lindholm | |
| 6,114,002 A | 9/2000 | Rinaldo | |
| 6,120,872 A | 9/2000 | Deshon | |
| 6,171,269 B1 | 1/2001 | Norin | |
| 6,190,551 B1 | 2/2001 | Nelson et al. | |
| 6,292,957 B1 | 9/2001 | Thompson | |
| 6,343,774 B1 | 2/2002 | Thomas et al. | |
| 6,963,271 B1 * | 11/2005 | Fyffe | ........................ 340/309.2 |
| 6,991,842 B2 * | 1/2006 | Hurwitz | ........................ 428/71 |

* cited by examiner

*Primary Examiner*—Tuan N Nguyen

(57) ABSTRACT

A therapeutic floor mat system and method are disclosed. A system incorporating teachings of the present disclosure may include, for example, a mat having an aromatherapy cavity. The aromatherapy cavity may be formed to at least partially hold an aromatic substance. In some cases, the mat may be operational as a shower mat and may have a top surface with a shape that defines a perimeter, and a bottom surface spaced apart from the top surface. Depending upon design detail, the aromatherapy cavity may be at least partially located beneath the top surface.

12 Claims, 4 Drawing Sheets

THERAPEUTIC FLOOR MAT SYSTEM AND METHOD

FIELD OF THE DISCLOSURE

The present disclosure relates to floor mats and more particularly to a therapeutic floor mat system and method.

BACKGROUND

Floor mats serve several functions and can be found in various locations. Many automobiles have floor mats that help keep the carpet beneath the mat protected from dirt and moisture, which might otherwise be tracked into the automobile by the driver and passengers. Floor mats can often be found at the ingress points of homes and offices. Similar to automobile floor mats, these doormats usually help ensure that dirt and moisture is not brought within a premises. Floor mats also appear in bathrooms and help protect against both slipping and the spread of germs. In practice, bathroom floor mats may be found on the bathroom floor, within a bathtub, or in a shower stall. Though floor mats are very prevalent in modern life, there are several ways in which modern floor mats may be improved to provide significant advantages.

BRIEF DESCRIPTION OF THE DRAWINGS

A more complete understanding of the present teachings and advantages associated therewith may be acquired by referring to the following description taken in conjunction with the accompanying drawings, in which like reference numbers indicate like features, and wherein.

DETAILED DESCRIPTION OF THE DRAWINGS

The following discussions focuses on adding therapeutic functionality to a floor mat. While the primary implementation discussed below includes a particular type of mat, a shower mat, the teachings should not be understood to apply solely to shower mats. The teachings may have much broader applicability. In other words, the focus maintained in the following discussion is not meant to limit the teachings.

Figure 1:
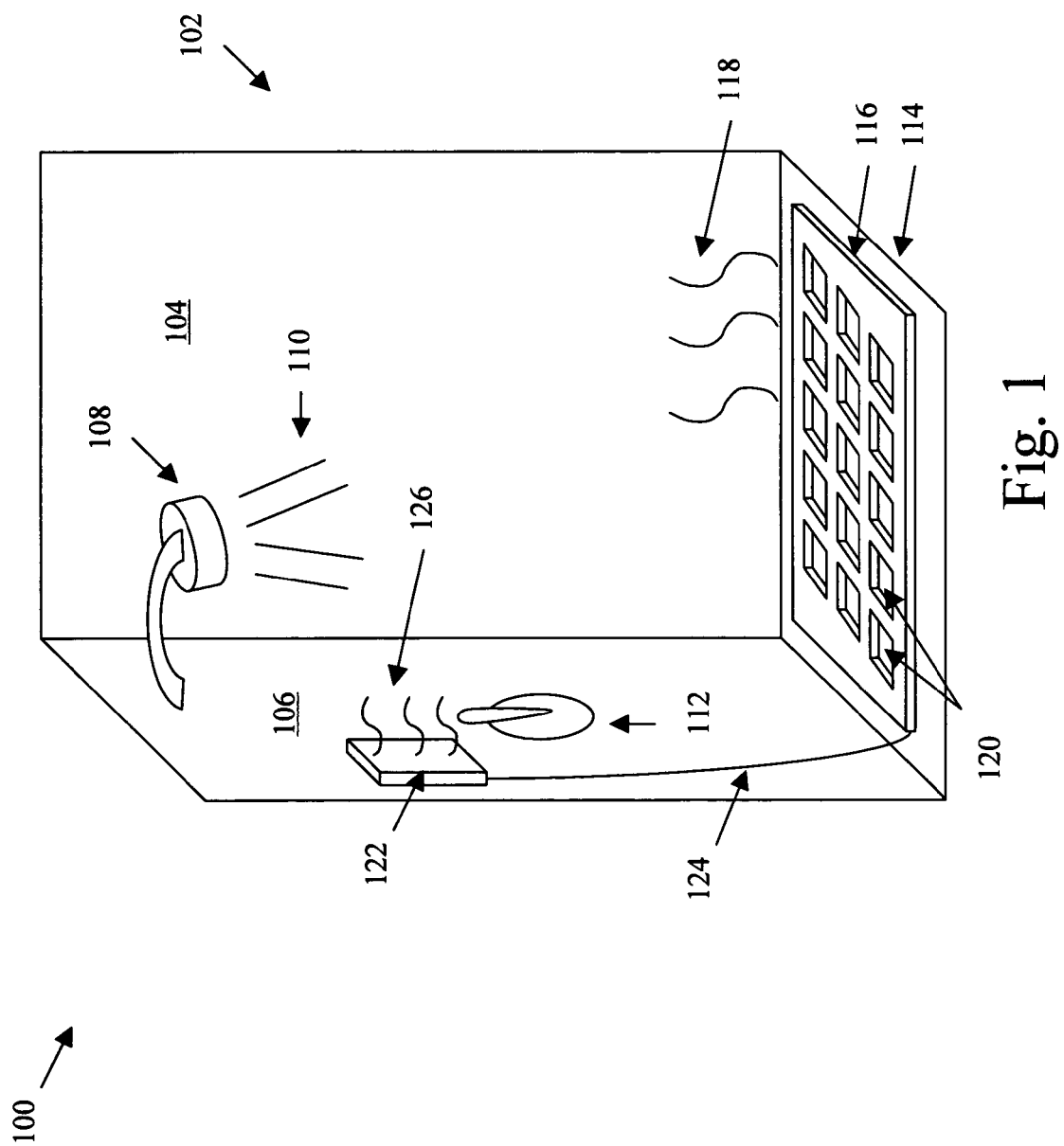
FIG. 1 depicts a therapeutic shower mat system incorporating teachings of the present disclosure to provide a user with an aromatherapy shower.

As indicated above, FIG. 1 depicts a therapeutic shower mat system 100 incorporating teachings of the present disclosure to provide a user with an aromatherapy shower. The aromatherapy shower may be one in which a person taking a shower enjoys an aroma, smell, odor, aromatic, fragrance, scent, etc. while showering. As used herein, aromatic and aromatic substances should not be limited to aromatic compounds as that term is understood in the field of organic chemistry. While a system designer may elect to use an organic like the oils of bitter almonds, wintergreen, the turpentine, the balsams, camphors, etc., the designer may not necessarily be limited to these.

As shown, system 100 includes a shower stall 102 having a generally square floor area. Shower walls 104 and 106 are also depicted along with showerhead 108, which extends from shower wall 106. As depicted, showerhead 108 is dispensing water 110 in a downward direction. In the system depicted, shower stall 102 includes a water temperature control dial 112, which may be used to control water flow volume and/or water temperature.

As depicted, dial 112 is set such that water 110 is at approximately 100° F. Depending on the preferences of a user, the water temperature of water 110 may vary a great deal. An exemplary range of water temperatures may be 60° F. to 110° F. Whatever the temperature, water 110 may fall to shower floor 114 before exiting shower stall 102 via a floor drain. As shown, system 100 may include a shower mat 116 resting on floor 114. In some cases, a bottom portion of mat 116 may include a mechanism that keeps mat 116 from sliding around on floor 114. The bottom portion may also include drainage channels that allow water to move under mat 116 to the floor drain.

In the depicted embodiment, mat 116 may be a therapeutic mat that is designed to release a fragrance when exposed to heat, water, the weight of a user, and/or some other release indicator or mechanism. Mat 116 may also be capable of releasing an anti-fungal element. For example, mat 116 may contain a substance that helps stop the spread of problematic disorders like athlete's foot. As shown, mat 116 includes an aromatic substance that at least partially volatilizes in the presence of heat. As hot water 110 falls on mat 116, volatiles may be released that carry a pleasing and relaxing odor, depicted as release 118. In practice, release 118 may be carried on the vapor or steam that rises during a hot shower, and water 110 falling on mat 116 may be routed through openings 120 and onto a floor drain for removal from stall 102.

While determining what qualifies as a pleasing or relaxing odor may be user-dependent, some exemplary odors may be an incense odor, a sandalwood odor, a rose odor, a basil odor, a rosemary odor, a dogwood odor, a lily odor, a sage odor, a pine odor, a mint odor, a eucalyptus odor, a jasmine odor, a lilac odor, a lavender odor, a floral odor, a spice odor, or a citrus odor. In some cases, a user may desire some combination of these and other odors.

Referring back to FIG. 1, shower stall 102 may also include a release mechanism 122. As depicted, mat 116 has two aromatherapy cavities formed to at least partially hold an aromatic substance. One of the cavities may be included within mat 116 itself and an other may be included within mechanism 122. In practice, mechanism 122 may be integrated with mat 116 via link 124. Though mechanism 122 is shown as being attached to wall 106, mechanism 122 may be located in other places and secured in place using several techniques. For example, mechanism 122 may rest on the floor, be attached to the ceiling, or attached to other walls. Depending upon design detail, mechanism 122 may adhere to a location, simply rest on a location, and/or hang from a location. For example, mechanism 122 may hang from showerhead 108 or dial 112.

Wherever located, link 124 may "communicate" to mechanism 122 that a user is in and/or using shower stall 102. For example, link 124 may include a pick-up that recognizes when a user is standing on mat 116, when water is flowing, when hot water contacts mat 116, and/or some other indicator of use. If stall 102 is in use, mechanism 122 may output a release 126. Depending upon design decisions, mechanism 122 may, for example, operate as a mister. Mechanism 122 may also be designed to apply heat to an aromatic substance that volatilizes in the presence of heat. However operated, mechanism 122 and/or an aromatherapy cavities included within mat 116 itself may provide a user of shower stall 102 with an aromatherapy shower experience.

Figure 2:
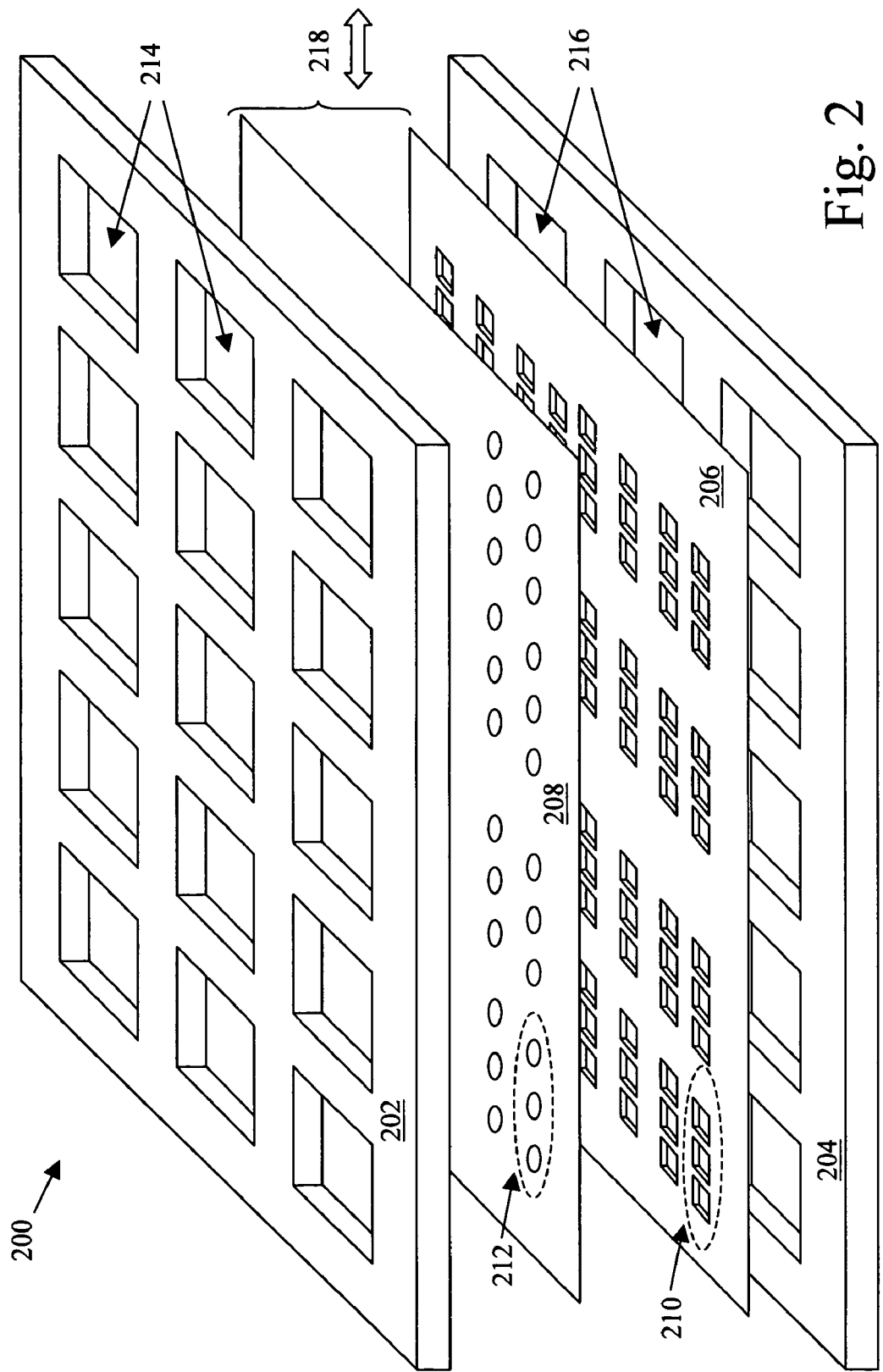
FIG. 2 depicts a mat system supporting interchangeable aromatherapy inserts in accordance with the present teachings.

As indicated above, FIG. 2 depicts a mat system 200 supporting interchangeable aromatherapy inserts in accordance with the present teachings. As shown, system 200 includes a layered design. System 200 has an upper layer 202 and a lower layer 204, which may be attached to one another in a number of ways. For example, layers 202 and 204 may be adhesively connected along their respective perimeters. Depending upon design concerns, layers 202 and 204 may be formed of similar and/or different materials such as a plastic substance, a rubberized substance, a ceramic substance, a natural substance like wood or fibers, some other functional substance, and/or a composite or combination of materials. Disposed between layers 202 and 204 may be an interchangeable insert 218. As indicated in FIG. 2 by a two-headed arrow, insert 218 may be placed into an aromatherapy cavity at least partially formed between layers 202 and 204.

An aromatherapy cavity may include an opening that accepts inserts like insert 218. Aromatherapy cavities may also include voids and/or reservoirs that hold an aromatic substance. As shown in FIG. 2, insert 218 may include a reservoir sheet 206 and a dispensing sheet 208. Reservoir sheet 206 may include several voids 210 configured to hold an aromatic substance. The aromatic substance may take several forms. For example, the aromatic substance may include a perfumed oil incorporated with a suitable carrier such as a solid, a liquid, a gel, a bead, and/or a capsulate. Other carrier material may include a porous material imbued with, impregnated with, and/or containing a scent.

In the depicted system 200, the carrier may be a gel composition disinclined to separate into distinct physical phases when heated. Example gel compositions include a gel agent such as a hydroxypropyl cellulose or a fumed silica mixed with a desired oil. In practice, the desired oil may make up as much as 95% of the gel composition. Though the perfumed oil may make up a large percentage of the gel composition, the relative pungency of a given gel composition may be managed through a diluting of the oil. For example, if a given gel composition seems overly intense, the perfume may be diluted with a solvent like dipropylene glycol or triethyl citrate.

Whatever the make up of a given aromatic substance, voids 210 may be utilized to hold the substance. Similarly, dispensing sheet 208 may act as a "lid" for voids 210. As depicted, sheet 208 includes several dispensing voids 212. Dispensing voids 212 may be apertures that have a top opening, which is depicted in FIG. 2. Voids 212 may be three-dimensional and extend through sheet 208. Moreover, voids 212 may have a tapering cross section that yields a wider aperture opening on top and a narrower bottom portion. In practice, the voids may be open at the bottom and may serve a capillary function. Placing a small opening closer to voids 210 may help sheet 208 function as a "lid" to voids 210. And, placing a larger opening at a top of void 212 may help sheet 208 to more effectively dispense a fragrance associated with a given aromatic substance.

In operation, hot water falling on system 200 may pass through openings 214 and 216. The hot water may cause aromatic substances maintained in voids 210 to volatilize, and volatiles may be released into an ambient for enjoyment by a user. In the depicted system 200, a top surface of the layered mat may include both portions of upper layer 202 and portions of dispensing sheet 208. As such, the top surface of system 200 may not be co-planar. In the depiction of FIG. 2, openings 214 expose at least some of dispensing sheet 208 and allow portions of dispensing sheet 208 to be on the top surface of system 200.

Figure 3:
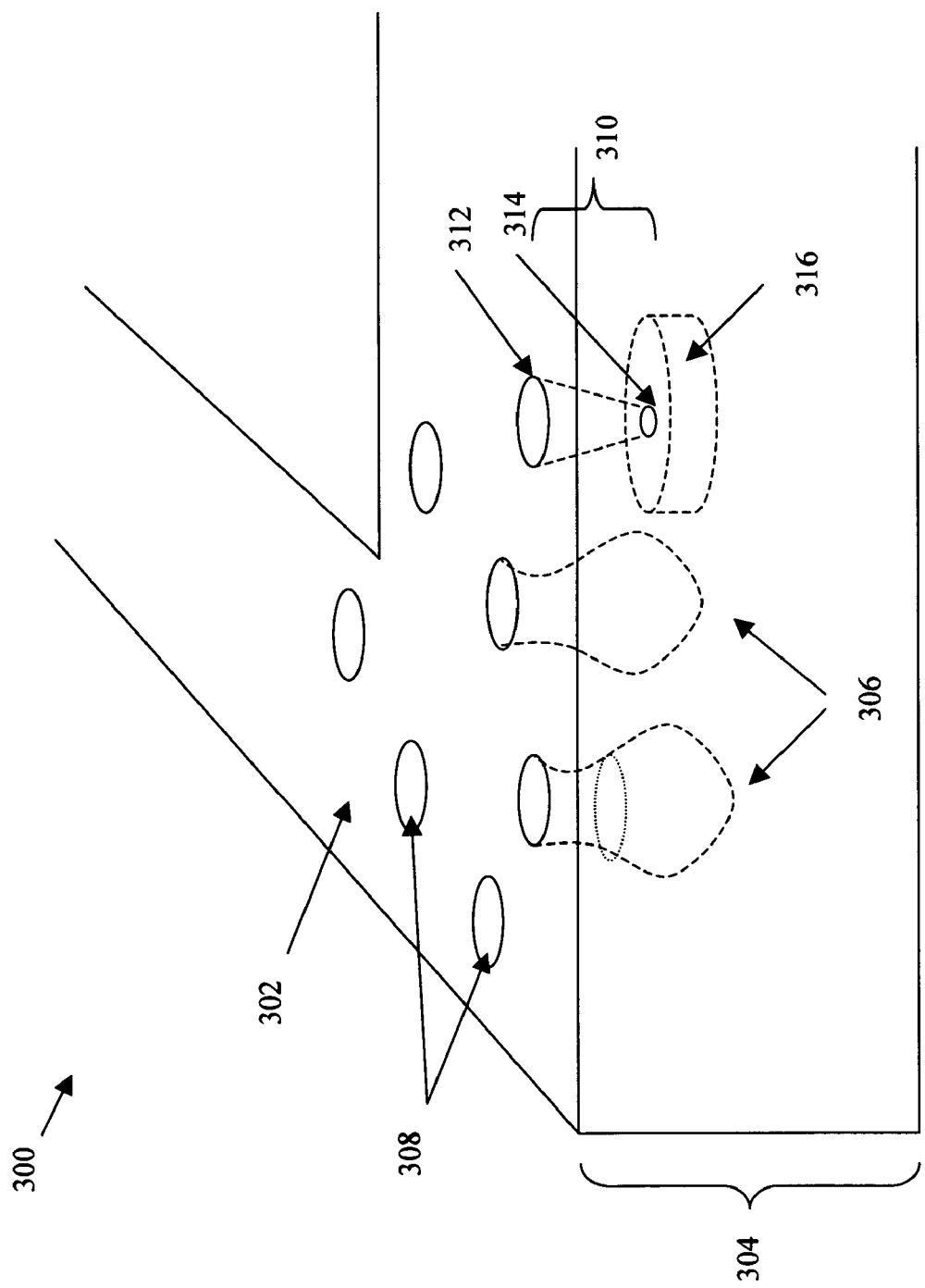
FIG. 3 shows a representation of a magnified view of a mat incorporating teachings of the present disclosure.

As indicated above, FIG. 3 shows a representation of a magnified view of a mat 300 incorporating teachings of the present disclosure. Mat 300 includes a user facing surface 302, which may be formed to present a comfortable and non-slip surface to a user. As shown, mat 300 has a thickness indicated by numeral 304 and several cavities 306 formed to hold an aromatic substance. In practice, the aromatic substance may be placed into cavities 306 in several ways. Mat 300 may be exposed to, sprayed with, and/or dipped into, for example, a volume of the aromatic substance. Such a process may allow cavities 306 to fill with an aromatic substance.

When in use, mat 300 may release pleasant odors through apertures 308. The release may be triggered in several ways. For example, the weight of a user may crush a cavity and cause the expulsion of an aromatic substance. Similarly, cavities 306 may be exposed to heat, and volatiles of an aromatic substance may be released via apertures 308. However released, a given aromatic substance may be designed such that it readily volatilizes at or around some selected temperature and/or pressure. For example, the substance may volatilize near room temperature. As such, simply forcing the substance from its cavity to expose the substance to ambient air may start volatilization. The substance may also be designed to volatilize at slightly elevated temperatures like those associated with hot water. The substance may also be designed to volatilize at higher temperatures. For example, mechanism 122 of FIG. 1 may include a heater that generates a higher temperature. In practice, this heater, could be for example, battery powered. As shown, apertures 308 may be naturally occurring or man-made voids present within a substance forming a portion of mat 300.

In some cases, a conically shaped void 310 may be used. Void 310 may extend from a user-facing surface 302 to an aromatic insert 316. As shown, void 310 has a larger opening 312 at user facing surface 302 and a narrower opening 314 at an interface with aromatic insert 316. Such a design may help extend the effective life of an aromatic substance. The conical void may help hold the substance in place and moderate the release of pleasant odors.

Figure 4:
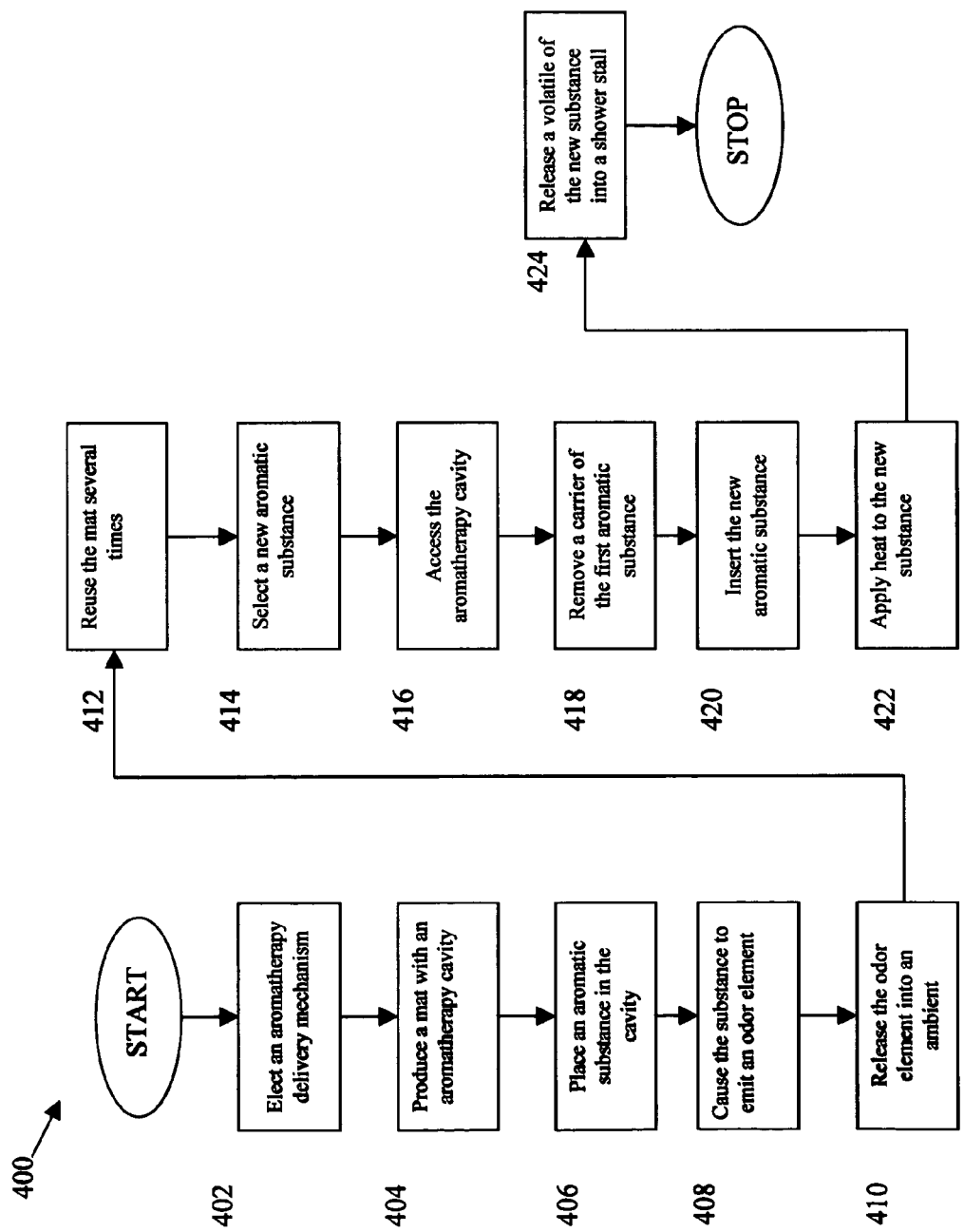
FIG. 4 illustrates a flow chart depicting a method incorporating teachings of the present disclosure to provide a user with an aromatherapy shower.

As indicated above, FIG. 4 illustrates a flow chart depicting a method 400 incorporating teachings of the present disclosure to provide a user with an aromatherapy shower. Method 400 may begin at step 402 where an aromatherapy delivery mechanism is selected. The mechanism may include, for example, a heat release mechanism, a compression release mechanism, a mister, and/or some other mechanism. Moreover, the mechanism may be located in one or more positions relative to a given mat. For example, the mechanism may be located within a mat and/or external to a mat as shown by mechanism 122 of FIG. 1. The mechanism may be configured such that a fragrance is released from above the mat, below the mat, beside the mat, within the mat, external to the mat, and/or some combination thereof.

At step 404, a mat may be produced that effectuates the decision made in step 402. And, at step 406 an aromatic substance may be placed in a cavity designed to hold the substance. The way in which the substance is placed may depend on a given mat's design. In some cases, a mat may include voids that are "loaded" with a substance through exposure to the substance. A mat may accept an insert or a liquid and/or gel filling of an associated vessel. A manufacturer may load a mat, and/or a user may load a mat.

However loaded, method 400 may progress to step 408 where something causes the substance to emit an odor. At step 410, the odor may be released into an ambient environment, which may be for example, a car's interior, a shower stall, a bathroom, etc. The mat may be reused several times at step 412. Reuse may stop, for example, if a therapeutic effect of the mat is waning. The aromatic substance may need to be recharged. A user may desire a new and/or different odor. Whatever the cause, a new aromatic substance may be selected at step 414 and an aromatherapy cavity may be accessed at step 416. The accessing may be by a user, a delivery mechanism, and/or some other appropriate option.

However accessed, a carrier of a first aromatic substance may be removed at step 418 and a new one inserted at step 420. At step 422, heat may be applied to the new aromatic substance, and a volatile may be released into an ambient at step 424. Method 400 may then progress to stop. Though the steps of method 400 are depicted in sequential order, the order of the steps may be changed. Moreover, various portions of method 400 may be performed by one or more entities, removed, added, and/or looped without departing from the teachings disclosed herein.

Although the disclosed embodiments have been described in detail, it should be understood that various changes, substitutions and alterations can be made to the embodiments without departing from the spirit and scope of the teachings included herein. The benefits, advantages, solutions to problems, and any element(s) that may cause any benefit, advantage, or solution to occur or become more pronounced are not to be construed as a critical, required, or essential features or elements of the present invention. Accordingly, the present invention is not intended to be limited to the specific form set forth herein, but on the contrary, it is intended to cover such alternatives, modifications, and equivalents, as can be reasonably included within the spirit and scope of the claims below.

What is claimed is:

1. A therapeutic floor mat system, comprising:
   a mat having a top, a bottom configured to rest on a surface, a plurality of openings in the mat to allow water falling on the mat to be routed through the mat and on to a floor drain for removal, the mat further having a thickness between the top and the bottom, the thickness including a plurality of aromatherapy cavities at least partially located between the top and the bottom each of which is in communication with an aperture in the top; and
   wherein a first portion of the plurality of aromatherapy cavities each includes a reservoir formed to at least partially hold an aromatic substance that releases upwardly through the corresponding aperture and a second portion of the plurality of aromatherapy cavities each includes an aromatic insert housed in the thickness and a conical void extending from the aromatic insert to the top, the conical void having a larger opening at the top than at an interface within the aromatic insert.

2. The system of claim 1, further comprising the aromatic substance, wherein the aromatic substance at least partially volatilizes in response to an application of heat.

3. The system of claim 1, further comprising the aromatic substance, wherein the aromatic substance releases in response to a crushing of the aromatherapy cavity.

4. The system of claim 1, further comprising the aromatic substance, wherein the aromatic substance comprises a gel composition disinclined to separate into distinct physical phases when heated.

5. The system of claim 1, further comprising the aromatic substance, wherein the aromatic substance comprises a gel composition, the gel composition comprising hydroxypropyl cellulose or fumed silica.

6. The system of claim 1, wherein the aromatic substance has an odor selected from a group consisting of an incense odor, a sandalwood odor; a rose odor, a basil odor, a rosemary odor, a dogwood odor, a lily odor, a sage odor, a pine odor, a mint odor, a eucalyptus odor, a jasmine odor, a lilac odor, a lavender odor, a floral odor, a spice odor, and a citrus odor.

7. The system of claim 1, wherein the aromatherapy cavity is configured to accept a replacing of the aromatic substance with a new aromatic substance.

8. The system of claim 1, wherein the mat is a shower mat.

9. A therapeutic shower mat, comprising:
   a top surface with a shape that defines a perimeter and having a first plurality of apertures;
   a bottom surface spaced apart from the top surface and having a second plurality of apertures to allow water falling on the therapeutic shower mat to be routed through the first and second plurality of apertures; and
   an aromatherapy cavity at least partially located beneath the top surface, the aromatherapy cavity formed to at least partially hold an aromatic substance that releases volatiles upwardly through the first plurality of apertures and to a user of the therapeutic shower mat in response to the water falling on the therapeutic shower mat, the aromatherapy cavity including a reservoir sheet including voids to hold the aromatic substance and a dispensing sheet including dispensing voids to dispense a fragrance associated with the aromatic substance, wherein each of the dispensing voids has a wider opening at a top portion than at a bottom portion of the dispensing void.

10. The system of claim 9, wherein the aromatherapy cavity is accessible to a user and the shower mat is configured to accept an insert comprising the aromatic substance.

11. The system of claim 9, wherein the top surface is not coplanar.

12. The system of claim 1, further comprising a release mechanism coupled to the mat and configured to release the aromatic substance when a user is on the mat.

* * * * *